US012697494B2

(12) United States Patent
Zhang et al.

(10) Patent No.: US 12,697,494 B2
(45) Date of Patent: Aug. 4, 2026

(54) VARIATION OF STIMULATION LOCATION IN AN ELECTRODE ARRAY IN A SPINAL CORD STIMULATION SYSTEM

(71) Applicant: Boston Scientific Neuromodulation Corporation, Valencia, CA (US)

(72) Inventors: Tianhe Zhang, Studio City, CA (US); Que T. Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 440 days.

(21) Appl. No.: 18/060,355

(22) Filed: Nov. 30, 2022

(65) Prior Publication Data

US 2023/0173283 A1     Jun. 8, 2023

Related U.S. Application Data

(60) Provisional application No. 63/264,825, filed on Dec. 2, 2021.

(51) Int. Cl.
*A61N 1/372*          (2006.01)

(52) U.S. Cl.
CPC ..... *A61N 1/37247* (2013.01); *A61N 1/37217* (2013.01)

(58) Field of Classification Search
None
See application file for complete search history.

(56) References Cited

U.S. PATENT DOCUMENTS 6,516,227 B1    2/2003   Meadows et al.
8,606,362 B2    12/2013  He et al.
8,620,436 B2    12/2013  Parramon et al.
9,295,840 B1    3/2016   Thacker et al.
10,716,937 B2   7/2020   Feldman et al.
(Continued)

FOREIGN PATENT DOCUMENTS

WO      2020/223165      11/2020
WO      2021/178105      9/2021

OTHER PUBLICATIONS

J.E. Gilbert et al., "Computational modeling predicts dorsal columns are involved in fast-acting sub-perception spinal cord stimulation (SCS)," Society for Neuroscience Abstract 2020 (submission) and Conference (2021).
(Continued)

*Primary Examiner* — Erica S Lee
(74) *Attorney, Agent, or Firm* — Lewis & Reese, PLLC

(57)          ABSTRACT

External system software is disclosed that automatically varies the location at which stimulation is applied to the patient in an Implantable Pulse Generator (IPG). Location variation occurs in an area defined with reference to the electrode array, and may occur randomly or via pre-defined path within the area. Preferably the area is defined around a single location deemed optimal for the patient. Parameters relating to the area and to how often the stimulation is moved can be set automatically or manually by a user of the software. The area may be defined using a probability distribution function (PDF) that tends to keep the stimulation at or close to an optimal position, while still allowing the location to be set anywhere in the area. The area may also be defined in the software using measured parameters indicative of the effectiveness of stimulation at different locations.

19 Claims, 13 Drawing Sheets

(56) References Cited

U.S. PATENT DOCUMENTS

| | | | |
|---|---|---|---|
| 10,792,491 B2 | 10/2020 | Feldman et al. | |
| 10,881,859 B2 | 1/2021 | Brill et al. | |
| 2009/0088818 A1* | 4/2009 | Starkebaum ....... | A61N 1/36007 |
| | | | 607/40 |
| 2011/0160800 A1* | 6/2011 | Dawant ................ | A61N 1/0534 |
| | | | 607/59 |
| 2013/0060302 A1 | 3/2013 | Polefko et al. | |
| 2013/0268019 A1* | 10/2013 | Gupta ................ | A61N 1/36067 |
| | | | 607/45 |
| 2015/0080982 A1 | 3/2015 | Funderburk | |
| 2015/0231402 A1 | 8/2015 | Aghassian | |
| 2015/0360038 A1 | 12/2015 | Zottola et al. | |
| 2016/0144194 A1* | 5/2016 | Roothans ............ | A61N 1/0534 |
| | | | 607/45 |
| 2016/0367822 A1 | 12/2016 | Parramon | |
| 2018/0071513 A1 | 3/2018 | Weiss et al. | |
| 2018/0071520 A1 | 3/2018 | Weerakoon et al. | |
| 2019/0269924 A1 | 9/2019 | Su et al. | |
| 2020/0254256 A1 | 8/2020 | Moffitt et al. | |
| 2023/0172479 A1* | 6/2023 | Verzal ................ | A61N 1/36078 |
| | | | 607/42 |

OTHER PUBLICATIONS

International Search Report and Written Opinion regarding corresponding PCT Application No. PCT/US2022/080675, mailed Mar. 14, 2023.

* cited by examiner

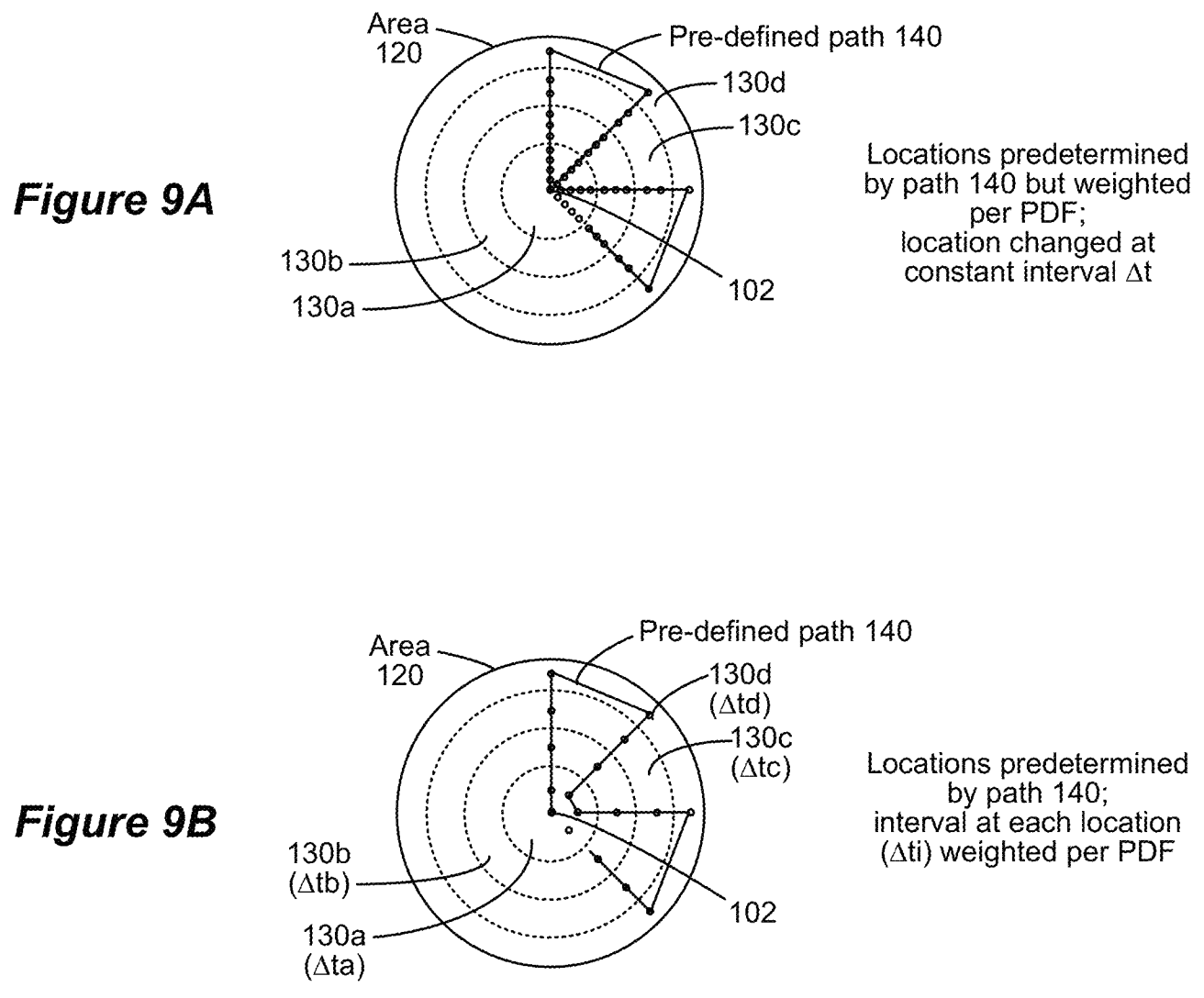

Pre-defined path 140

130d

130c

Locations predetermined by path 140 but weighted per PDF; location changed at constant interval $\Delta t$

102

Area 120

Pre-defined path 140

130d ($\Delta td$)

130c ($\Delta tc$)

Locations predetermined by path 140; interval at each location ($\Delta ti$) weighted per PDF

102

Area 120

130b ($\Delta tb$)

130a ($\Delta ta$)

*Figure 9B*

Locations randomized; location changed at constant interval Δt (no PDF)

Random path 125

102

Area 120

Locations predetermined by path 140; location changed at constant interval Δt (no PDF)

Pre-defined path 140

Area 120

Figure 13:
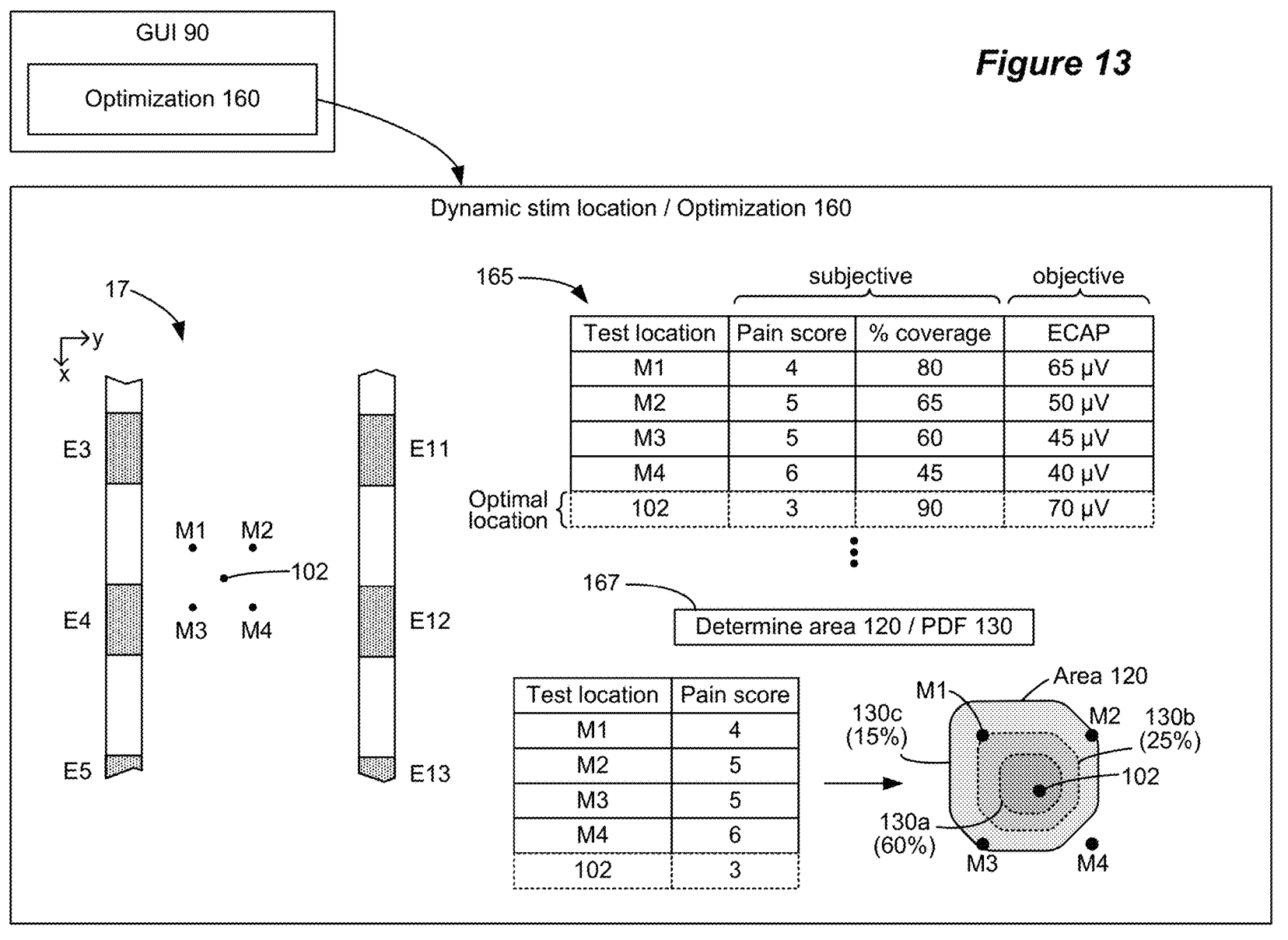

GUI 90

Optimization 160

Dynamic stim location / Optimization 160

165 —

| Test location | Pain score | % coverage | ECAP |
|---|---|---|---|
| M1 | 4 | 80 | 65 µV |
| M2 | 5 | 65 | 50 µV |
| M3 | 5 | 60 | 45 µV |
| M4 | 6 | 45 | 40 µV |
| 102 | 3 | 90 | 70 µV | subjective / objective

Optimal location

167 —

Determine area 120 / PDF 130

| Test location | Pain score |
|---|---|
| M1 | 4 |
| M2 | 5 |
| M3 | 5 |
| M4 | 6 |
| 102 | 3 |

Area 120

M2  130b (25%)
102
M4
130c (15%)
M1
130a (60%)
M3

E11
E12
E13

17

M2
102
M4
M1
M3

E3
E4
E5 y
x

VARIATION OF STIMULATION LOCATION IN AN ELECTRODE ARRAY IN A SPINAL CORD STIMULATION SYSTEM

CROSS REFERENCE TO RELATED APPLICATIONS

This is a non-provisional application of U.S. Provisional Patent Application Ser. No. 63/264,825, filed Dec. 2, 2021, which is incorporated herein by reference, and to which priority is claimed.

FIELD OF THE INVENTION

This application relates to Implantable Medical Devices (IMDs) generally, Spinal Cord Stimulators more specifically, and to methods of control of such devices.

INTRODUCTION

Implantable stimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible device case 12 that holds the circuitry and battery 14 necessary for the IPG to function. The IPG 10 is coupled to electrodes 16 via one or more electrode leads 15 that form an electrode array 17. The electrodes 16 are configured to contact a patient's tissue and are carried on a flexible body 18, which also houses the individual lead wires 20 coupled to each electrode 16. The lead wires 20 are also coupled to proximal contacts 22, which are insertable into lead connectors 24 fixed in a header 23 on the IPG 10, which header can comprise an epoxy for example. Once inserted, the proximal contacts 22 connect to header contacts within the lead connectors 24, which are in turn coupled by feedthrough pins through a case feedthrough to circuitry within the case 12, although these details aren't shown. Electrode array 17 can also be formed on a well-known paddle lead, although this detail isn't shown.

In the illustrated IPG 10, there are sixteen lead electrodes (E1-E16) split between two leads 15, with the header 23 containing a 2×1 array of lead connectors 24. However, the number of leads and electrodes in an IPG is application specific and therefore can vary. The conductive case 12 can also comprise an electrode (Ec). In a SCS application, the electrode leads 15 are typically implanted proximate to the dura in a patient's spinal column on the right and left sides of the spinal cord midline. The proximal electrodes 22 are tunneled through the patient's tissue to a distant location such as the buttocks where the IPG case 12 is implanted, at which point they are coupled to the lead connectors 24. In other IPG examples designed for implantation directly at a site requiring stimulation, the IPG can be lead-less, having electrodes 16 instead appearing on the body of the IPG for contacting the patient's tissue. The IPG leads 15 can be integrated with and permanently connected the case 12 in other IPG solutions. The goal of SCS therapy is to provide electrical stimulation from the electrodes 16 to alleviate a patient's symptoms, most notably chronic back pain.

IPG 10 can include an antenna 26a allowing it to communicate bi-directionally with a number of external devices, as shown in FIG. 4. The antenna 26a as depicted in FIG. 1 is shown as a conductive coil within the case 12, although the coil antenna 26a can also appear in the header 23. When antenna 26a is configured as a coil, communication with external devices preferably occurs using near-field magnetic induction. IPG 10 may also include a Radio-Frequency (RF) antenna 26b. In FIG. 1, RF antenna 26b is shown within the header 23, but it may also be within the case 12. RF antenna 26b may comprise a patch, slot, or wire, and may operate as a monopole or dipole. RF antenna 26b preferably communicates using far-field electromagnetic waves. RF antenna 26b may operate in accordance with any number of known RF communication standards, such as Bluetooth, Zigbee, WiFi, MICS, and the like.

Stimulation in IPG 10 is typically provided by pulses, as shown in FIG. 2. Stimulation parameters typically include a stimulation amplitude (I; whether current or voltage); the frequency (F) and pulse width (PW) of the pulses; the electrodes 16 activated to provide such stimulation; the polarity of such active electrodes, i.e., whether active electrodes are to act as anodes (that source current to the tissue) or cathodes (that sink current from the tissue); and the relative percentage of the amplitude that each active electrode should produce. These stimulation parameters taken together comprise a stimulation program that the IPG 10 can execute to provide therapeutic stimulation to a patient. A stimulation program can also comprise still further stimulation parameters, and may not necessarily include all of the stimulation parameters just listed.

In the example of FIG. 2, electrode E5 has initially been selected as an anode, and thus provides pulses which source a positive current of amplitude +I to the tissue. Electrode E4 has initially been selected as a cathode, and thus provides pulses which sink a corresponding negative current of amplitude −I from the tissue. This is an example of bipolar stimulation, in which only lead-based electrodes are used to provide stimulation to the tissue by forming one anode pole and one cathode pole in the electrode array 17. However, more than one electrode may act as an anode at a given time to form the anode pole, and more than one electrode may act as a cathode at a given time to form the cathode pole, as discussed further below. Furthermore, different numbers of poles can be used (e.g., tripole stimulation involving for example two anode poles flanking a cathode pole, quadripole stimulation, etc.).

IPG 10 includes stimulation circuitry 28 that can be programmed to produce the stimulation pulses at the electrodes as defined by the stimulation program, as shown in FIG. 3. Stimulation circuitry 28 can for example comprise the circuitry described in U.S. Patent Application Publications 2018/0071513 and 2018/0071520, or in USPs 8,606, 362 and 8,620,436. These references are incorporated herein by reference. Preferably, the stimulation circuitry 28 allows the magnitude and polarity of the current to be independently programmed at each of the electrodes. For example, to initially form the waveform shown in FIG. 2, a current source circuit coupled to electrode E4 (PDAC4) is programmed (per control signals I4p) to produce the desired amplitude +I, while a current sink circuit coupled to electrode E5 (NDAC5) is programmed (per control signals I5n) to produce the desired amplitude −I.

The pulses as shown in FIG. 2 are biphasic, comprising a first phase 30a, followed quickly thereafter by a second phase 30b of opposite polarity which reverses the direction of current flow through the tissue. As is known, biphasic pulses are useful in active charge recovery. For example, each electrodes' current path to the tissue may include a serially-connected DC-blocking capacitor 38 (FIG. 3) that which will charge during the first phase 30a, and be discharged (i.e., stored charge will be recovered) during the second phase 30b. In the example shown, the first and second phases 30a and 30b have the same duration and amplitude (although opposite polarities), which ensures the same amount of charge is passed during both phases. However, the second phase 30b may also be charged balance with the first phase 30a if the integral of the amplitude and durations of the two phases are equal in magnitude, as is well known. The width of each pulse, PW, is defined in FIG. 2 as the duration of first pulse phase 30a, although pulse width could also refer to the duration of both phases 30a and 30b (if the biphasic waveform is symmetric as shown) or the total duration of phases 30a and 30b as well. An interphase period (IP) may be provided between the two phases 30a and 30b during which no current is driven by the stimulation circuitry 28. Note that programming of the stimulation circuitry 28 during the second (recovery) pulse phase 30b would reverse the polarity of the current, with In4 and Ip5 programmed to cause NDAC4 and PDAC5 to set amplitude I in FIG. 3. Passive charge recovery may also occur, which does not involve the active driving of currents at the electrodes from the current source (PDACi) or sink (NDACi) circuitry, although this detail isn't shown. See, e.g., USPs 10,716,937 and 10,792,491 (discussing passive charge recovery).

Although not shown, stimulation can also be provided to a patient by an external trial stimulator (ETS), which allows stimulation to be tried on a prospective implant patient whose leads 15 have been implanted, but who has not yet received an implanted IPG 10. See, e.g., 9,259,574, disclosing a design for an ETS. The ETS generally mimics operation of the IPG 10 and includes similar stimulation circuitry 28 and antennas as necessary to communicate with and be programmed by other external devices discussed subsequently. As used herein, IPGs or implantable stimulation devices should be understood as including ETSs.

FIG. 4 shows various external systems 40, 50, and 60 that can wirelessly communicate data with the IPG 10 (which again can include an ETS). Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information, etc.

External controller 40 can be as described in U.S. Patent Application Publication 2015/0080982 for example, and may comprise a portable, hand-held controller dedicated to work with the IPG 10. External controller 40 may also comprise a general-purpose mobile electronics device such as a mobile phone which has been programmed with a Medical Device Application (MDA) allowing it to work as a wireless controller for the IPG 10, as described in U.S. Patent Application Publication 2015/0231402. External controller 40 includes a display 41 and a means for entering commands, such as buttons 42 or selectable graphical icons provided on the display 41. The external controller 40's user interface enables a patient to adjust stimulation parameters, although it may have limited functionality when compared systems 50 and 60, described shortly. The external controller 40 can have one or more antennas capable of communicating with the IPG 10. For example, the external controller 40 can have a near-field magnetic-induction coil antenna 44a capable of wirelessly communicating with the coil antenna 26a in the IPG 10. The external controller 40 can also have a far-field RF antenna 44b capable of wirelessly communicating with the RF antenna 26b in the IPG 10.

Clinician programmer 50 is described further in U.S. Patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 51, buttons 52, as well as other user-interface devices such as a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 56 coupleable to suitable ports on the computing device. The antenna used in the clinician programmer 50 to communicate with the IPG 10 can depend on the type of antennas included in the IPG 10. If the patient's IPG 10 includes a coil antenna 26a, wand 56 can likewise include a coil antenna 54a to establish near-field magnetic-induction communications at small distances. In this instance, the wand 56 may be affixed in close proximity to the patient, such as by placing the wand 56 in a belt or holster wearable by the patient and proximate to the patient's IPG 10. If the IPG 10 includes an RF antenna 26b, the wand 56, the computing device, or both, can likewise include an RF antenna 54b to establish communication with the IPG 10 at larger distances. The clinician programmer 50 can also communicate with other devices and networks, such as the Internet, either wirelessly or via a wired link provided at an Ethernet or network port.

External system 60 comprises another means of communicating with and controlling the IPG 10 via a network 65 which can include the Internet. The network 65 can include a server 66 programmed with communication and control functionality, and may include other communication networks or links such as WiFi, cellular or land-line phone links, etc. The network 65 ultimately connects to an intermediary device 62 having antennas suitable for communication with the IPG's antenna, such as a near-field magnetic-induction coil antenna 64a and/or a far-field RF antenna 64b. Intermediary device 62 may be located generally proximate to the IPG 10. Network 65 can be accessed by any user terminal 70, which typically comprises a computer device associated with a display 71. External system 60 allows a remote user at terminal 70 to communicate with and control the IPG 10 via the intermediary device.

FIG. 4 also shows circuitry 80 involved in any of external systems 40, 50, or 60. Such circuitry can include control circuitry 82, which can comprise any number of devices such as one or more microprocessors, microcomputers, FPGAs, DSPs, other digital logic structures, etc., which are capable of executing programs in a computing device. Such control circuitry 82 may contain or coupled with memory 84 which can store external system software 86 for controlling and communicating with the IPG 10, and for rendering a Graphical User Interface (GUI) 90 on a display (41, 51, 71) associated with the external system. In external system 60, the external system software 86 would likely reside in the server 66, while the control circuitry 82 could be present in either or both the server 66 or the terminal 70.

An example of GUI 90 renderable on an external system is shown in FIG. 5. One skilled in the art will understand that the particulars of the GUI 90 will depend on where external system software 86 is in its execution, which may depend on previous GUI selections the user has made. FIG. 5 shows the GUI 90 at a point allowing for the setting of stimulation parameters for the patient and for their storage as a stimulation program. To the left a program interface 91 is shown, which allows for naming, loading and saving of stimulation programs for the patient. Shown to the right is a stimulation parameters interface 92, in which specific stimulation parameters can be defined for a stimulation program. Values for stimulation parameters relating to the shape of the waveform (I; in this example, current), pulse width (PW, of either or both phases 30a and 30b), and frequency (F) are shown in a waveform parameter interface 93, including buttons the clinician can use to increase or decrease these values.

Stimulation parameters relating to the electrodes 16 that will receive the defined waveform are selectable in an electrode parameter interface 94. (As discussed shortly, electrode stimulation parameters may also be determined automatically by an electrode configuration algorithm operable in the external system software 86). The electrode parameter interface 94 allows different electrodes (including case electrode Ec) to be selected to receive stimulation, and to define the polarity of those electrodes (anode, cathode, off). The electrode parameter interface 94 further allows the relative percentage (X %) of the prescribed amplitude I to be defined at each electrode. This is particularly useful if the anodic or cathodic current is to be shared by more than one electrode at any given time: for example, if anode E1 receives 80%*+I and anode E2 receives 20%*+I; or if cathode E11 receives 30%*−I, cathode E12 receives 50%*−I, and cathode E6 receives 20%*−I. Such sharing of anodic (+I) and cathodic (−I) currents allows anode and cathode poles 89 to be formed whose positions in the electrode array 17 do not necessarily correspond to the physical positions of any particular electrode 16. As noted earlier, these poles 89 together comprise a bipole.

A leads interface 95 can display the various leads 15, or the electrode array 17 more generally, with the electrodes shown in proper position with respect to each other, for example, on the left and right sides of the spinal column. Anode (+) and cathode (−) poles 89 indicative of the specification stimulation may also be displayed in the leads interface 95 at a proper location in the electrode array 17. The position of these poles 89 may be set in accordance with the above-mentioned electrode configuration algorithm, which allows a position of a pole 93 to be determined from the active electrodes, their polarities, and their relative percentages. See U.S. Pat. No. 10,881,859 (discussing an electrode configuration algorithm). A cursor 96 (or other selection means such as a mouse pointer) can be used to move the poles 89 in the electrode array 17; to select particular electrodes or positions in the leads interface 95; and/or to otherwise navigate the GUI 90. The electrode configuration algorithm may operate in reverse to determine which electrodes to activate, and with which polarities and relative percentages, when the position of the one or more poles 89 is set or moved in the leads interface 95. The stimulation (i.e., poles 89) may also be moved in the electrode array using other GUI elements, such as direction arrows 97.

An advanced menu 98 can also be used (among other things) to define the relative durations and amplitudes of the pulse phases 30a and 30b, and to allow for other more advanced modifications, such as setting burst of pulses, setting a duty cycle (on/off time) for the stimulation pulses, and setting a ramp-up time over which stimulation reaches its programmed amplitude (I), etc. A mode menu 99 allows the clinician to choose different modes for determining stimulation parameters.

SUMMARY

A method is disclosed for providing stimulation in a stimulator device having a plurality of electrode nodes each coupled to an electrode in contact with a patient's tissue, wherein the electrodes form an electrode array. The method may comprise: determining a first location in the electrode array to apply the stimulation for the patient; determining a function, wherein the function indicates probabilities of positioning the stimulation at locations within an area defined around the first location; and applying the stimulation to the patient using the electrode array, wherein location of the stimulation is moved over time within the area in accordance with the function to locate the stimulation in accordance with the probabilities.

In one example, the function indicates at least two different probabilities. In one example, the probabilities are greater than 0% and less than 100%. In one example, the probabilities preferentially locate the stimulation proximate to the first location when the stimulation is moved within the area. In one example, the probabilities set a relative time at which stimulation will be applied at locations within the area. In one example, the stimulation is automatically moved within the area. In one example, the stimulation is moved at a constant time interval within the area. In one example, the stimulation is moved randomly among the locations within the area. In one example, the stimulation is moved to the locations within the area in accordance with a pre-defined path. In one example, the first location is at a center of the area. In one example, the area is circular. In one example, the area is elongated in a rostral-caudal or a medio-lateral direction. In one example, the function comprises sub-areas within the area each associated with one of the probabilities. In one example, the function comprises a mathematical function that determines the probabilities. In one example, the stimulation moved within the area is sub-perception. In one example, the first location is determined to provide effective therapeutic results for the patient. In one example, the function is determined using measurements indicative of the efficacy of the stimulation for the patient. In one example, the measurements are taken by locating the stimulation at a plurality of test locations in the electrode array. In one example, a plurality of the measurements are taken at each of the test locations. In one example, the measurements are subjective and based on patient feedback. In one example, the measurements are objective and measured using the stimulator device. In one example, the function is determined in an external system in communication with the stimulator device, and wherein information indicative of the function is transmitted to the stimulator device to enable the stimulator device to move the location of the stimulation within the area in accordance with the PDF. In one example, the function is determined in an external system in communication with the stimulator device, and wherein the locations to which the stimulation are moved are periodically transmitted to the stimulator device to enable the stimulator device to move the location of the stimulation within the area in accordance with the function. In one example, the method further comprises updating the function, wherein the location of the stimulation is moved over time within the area in accordance with the updated function to locate the stimulation in accordance with the probabilities.

A system is disclosed, which may comprise: an external system configured to control a stimulator device having a plurality of electrode nodes each coupled to an electrode contactable with a patient's tissue, wherein the electrodes form an electrode array, the external system comprising control circuitry configured to render a graphical user interface (GUI) to allow a user to: determine a first location in the electrode array to apply the stimulation for the patient; determine a function, wherein the function indicates probabilities of positioning the stimulation at locations within an area defined around the first location; and transmit information to the stimulator device to enable to stimulator device to apply the stimulation to the patient using the electrode array by moving the location of the stimulation over time within the area in accordance with the function to locate the stimulation in accordance with the probabilities.

In one example, the function indicates at least two different probabilities. In one example, the probabilities are greater than 0% and less than 100%. In one example, the probabilities preferentially locate the stimulation proximate to the first location when the stimulation is moved within the area. In one example, the probabilities set a relative time at which stimulation will be applied at locations within the area. In one example, the information enables the stimulator device to automatically move the location of the stimulation within the area. In one example, the information enables the stimulator device to move the location of the stimulation at a constant time interval within the area. In one example, the information enables the stimulator device to randomly move the location of the stimulation within the area. In one example, the GUI further allows the user to define a pre-defined path, wherein the information enables the stimulator device to move the location of the stimulation in accordance with the pre-defined path within the area. In one example, the first location is at a center of the area. In one example, the area is circular. In one example, the GUI further allows the user to elongate the area in a rostral-caudal or a medio-lateral direction. In one example, the function comprises sub-areas within the area each associated with one of the probabilities. In one example, the function comprises a mathematical function that determines the probabilities. In one example, the stimulation moved within the area over time is sub-perception. In one example, the first location is determined to provide effective therapeutic results for the patient. In one example, the GUI further receives measurements indicative of the efficacy of the stimulation for the patient, wherein the function is determined in the external system using the measurements. In one example, the measurements are taken by locating the stimulation at a plurality of test locations in the electrode array. In one example, a plurality of the measurements are taken at each of the test locations. In one example, the measurements are subjective and based on patient feedback. In one example, the measurements are objective and measured using the stimulator device. In one example, the system further comprises the stimulator device. In one example, the transmitted information comprises the function, wherein the stimulator device is configured to determine from the transmitted information the locations to which the stimulation will be moved within the area. In one example, the external system is configured to determine the locations to which the stimulation will be moved within the area, and wherein the transmitted information comprises the determined locations. In one example, the GUI further allow the user to: update the function; and transmit information to the stimulator device to enable to stimulator device to apply the stimulation to the patient using the electrode array by moving the location of the stimulation over time within the area in accordance with the updated function to locate the stimulation in accordance with the probabilities.

A non-transitory computer readable medium is discloses comprising instructions executable on an external system configured to control a stimulator device having a plurality of electrode nodes each coupled to an electrode contactable with a patient's tissue, wherein the electrodes form an electrode array, the instructions when executed rendering a graphical user interface (GUI) to allow a user to: determine a first location in the electrode array to apply the stimulation for the patient; determine a function, wherein the function indicates probabilities of positioning the stimulation at locations within an area defined around the first location; and transmit information to the stimulator device to enable to stimulator device to apply the stimulation to the patient using the electrode array by moving the location of the stimulation over time within the area in accordance with the function to locate the stimulation in accordance with the probabilities.

BRIEF DESCRIPTION OF THE DRAWINGS

FIGS. 9A and 9B show different examples of use of a PDF to affect stimulation at different locations along a pre-defined path within an area.

FIG. 13 shows a GUI used to optimize an area and/or a PDF for a patient using various measurements.

DETAILED DESCRIPTION

While Spinal Cord Stimulation (SCS) therapy can be an effective means of alleviating a patient's pain, such stimulation can also cause paresthesia. Paresthesia—sometimes referred to a "supra-perception" or supra-threshold therapy—is a sensation such as tingling, prickling, heat, cold, etc. that a patient can feel as a result of the stimulation. Generally, the effects of paresthesia are mild, or at least are not overly concerning to a patient. Moreover, paresthesia is generally a reasonable tradeoff for a patient whose chronic pain has now been brought under control by SCS therapy. Some patients even find paresthesia comfortable and soothing.

Nonetheless, at least for some patients, SCS therapy would ideally provide complete pain relief without paresthesia—what is often referred to as "sub-perception" or sub-threshold therapy that a patient cannot feel. Effective sub-perception therapy may provide pain relief without paresthesia by issuing stimulation pulses at higher frequencies (e.g., 10 kHz). Unfortunately, such higher-frequency stimulation may require more power, which tends to drain the battery 14 of the IPG 10. See, e.g., U.S. Patent Application Publication 2016/0367822. If an IPG's battery 14 is a primary cell and not rechargeable, high-frequency stimulation means that the IPG 10 will need to be replaced more quickly. Alternatively, if an IPG battery 14 is rechargeable, the IPG 10 will need to be charged more frequently, or for longer periods of time. Either way, the patient is inconvenienced.

Figure 5:
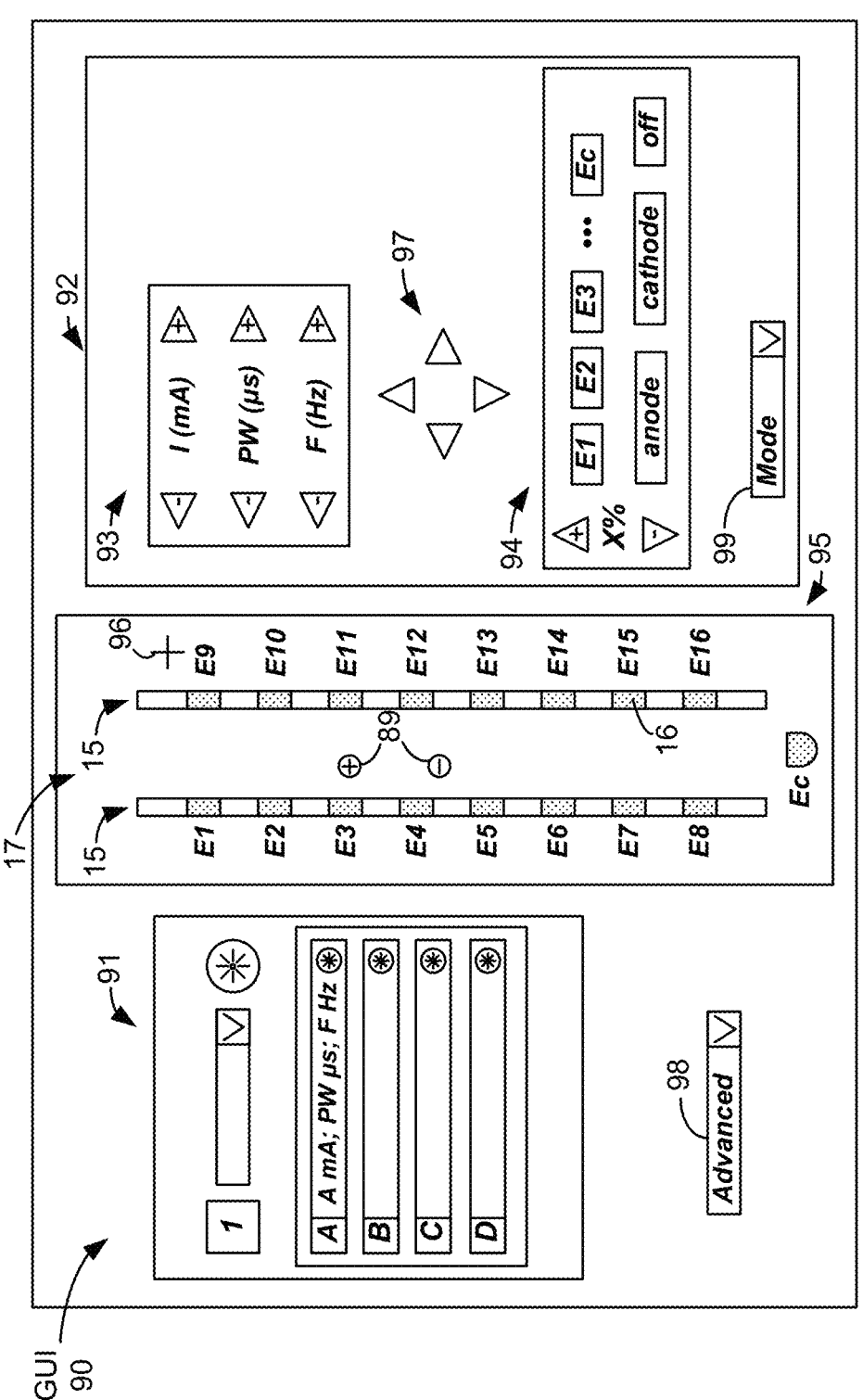
FIG. 5 shows a Graphical User Interface (GUI) of an external system for setting or adjusting stimulation parameters, in accordance with the prior art.

In an SCS application, it may therefore be desirable to determine a sub-perception stimulation program that will be effective for a given patient. A significant part of determining an effective stimulation program is to determine a "sweet spot" for stimulation in each patient, i.e., to select a proper location for the stimulation in the electrode array 17. As explained further below, this location is dictated by which electrodes in the array are active, and with what polarities and relative amplitudes (X %). Locating stimulation such that it is optimal to treat a neural site of pain in the patient can involve moving the location of the stimulation in the electrode array 17 until best therapeutic results are realized. This process can be described as "sweet spot searching," and may be affected as a mode selection 90 (FIG. 5) in the GUI 64.

As described in Int'l (PCT) Patent Application Publication No. WO 2021/178105, which is hereby incorporated by reference in its entirety, sweet spot searching may be difficult when sub-perception therapy is desired, because the patient does not feel the stimulation, and therefore may not easily feel whether stimulation provided at various locations in the electrode array 17 is well "covering" or masking his pain.

Figure 1:
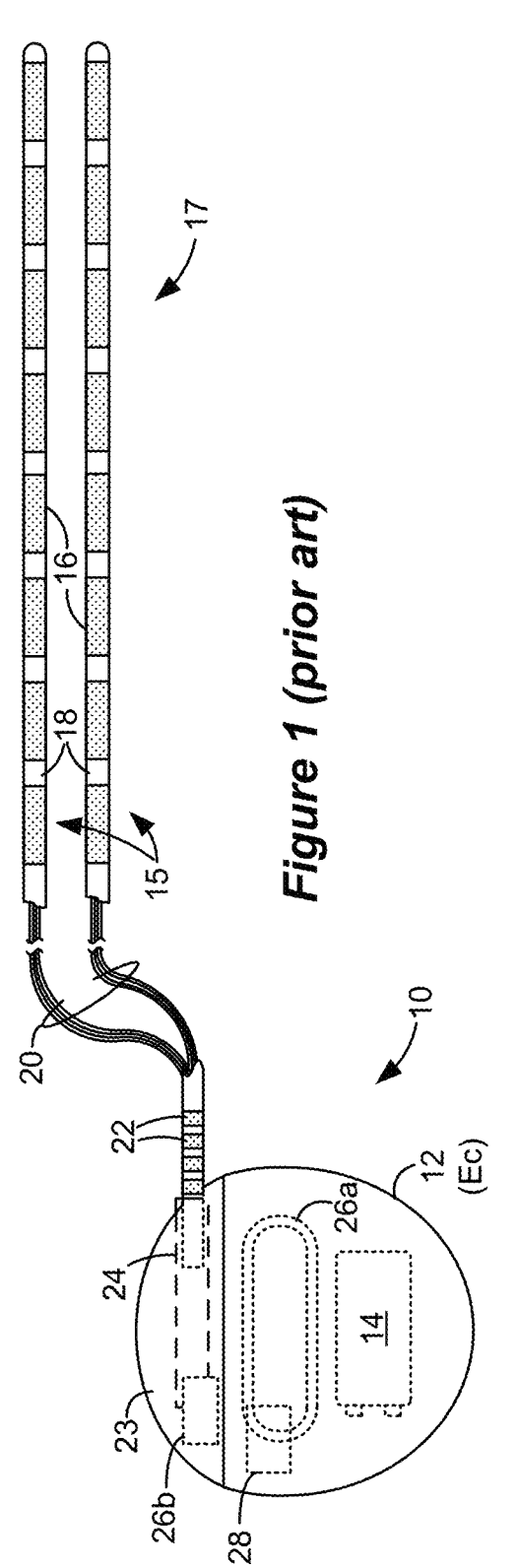
FIG. 1 shows an Implantable Pulse Generator (IPG) useable for Spinal Cord Stimulation (SCS), in accordance with the prior art.
Figure 2:
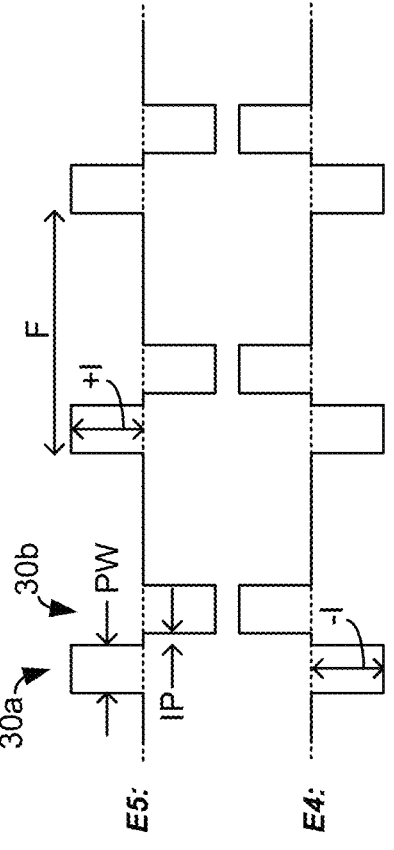
FIG. 2 shows an example of stimulation pulses producible by the IPG, in accordance with the prior art.

The '105 Publication discloses an approach in which supra-perception sweet spot searching is performed to determine an optimal location for stimulation in the electrode array 17, followed by the use of sub-perception stimulation at that determined location. Use of supra-perception stimulation during the sweet spot search greatly accelerates determination of an optimal location, because the patient can quickly feel whether stimulation seems to be covering his pain at each new location tested during the sweet spot search. Once a best location for stimulation is determined, stimulation parameters (most preferably, amplitude) can be reduced at that location to sub-perception levels. Because the electrodes used to provide stimulation at this best location are known to be well recruiting the neural site of the patient's pain, the application of sub-perception stimulation at that location is more likely to have immediate effect, and will quickly "wash in" to provide good therapeutic results, such as in one hour or less, ten minutes or less, or one minute or less. In short, effective sub-perception therapy can be achieved more quickly for the patient when supra-perception sweet spot searching is utilized. Preferably, supra-perception sweet spot searching occurs using symmetric biphasic pulses (see FIG. 2) occurring at low frequencies—such as between F=40 and 200 Hz in one example.

Figures 6A, 6B:
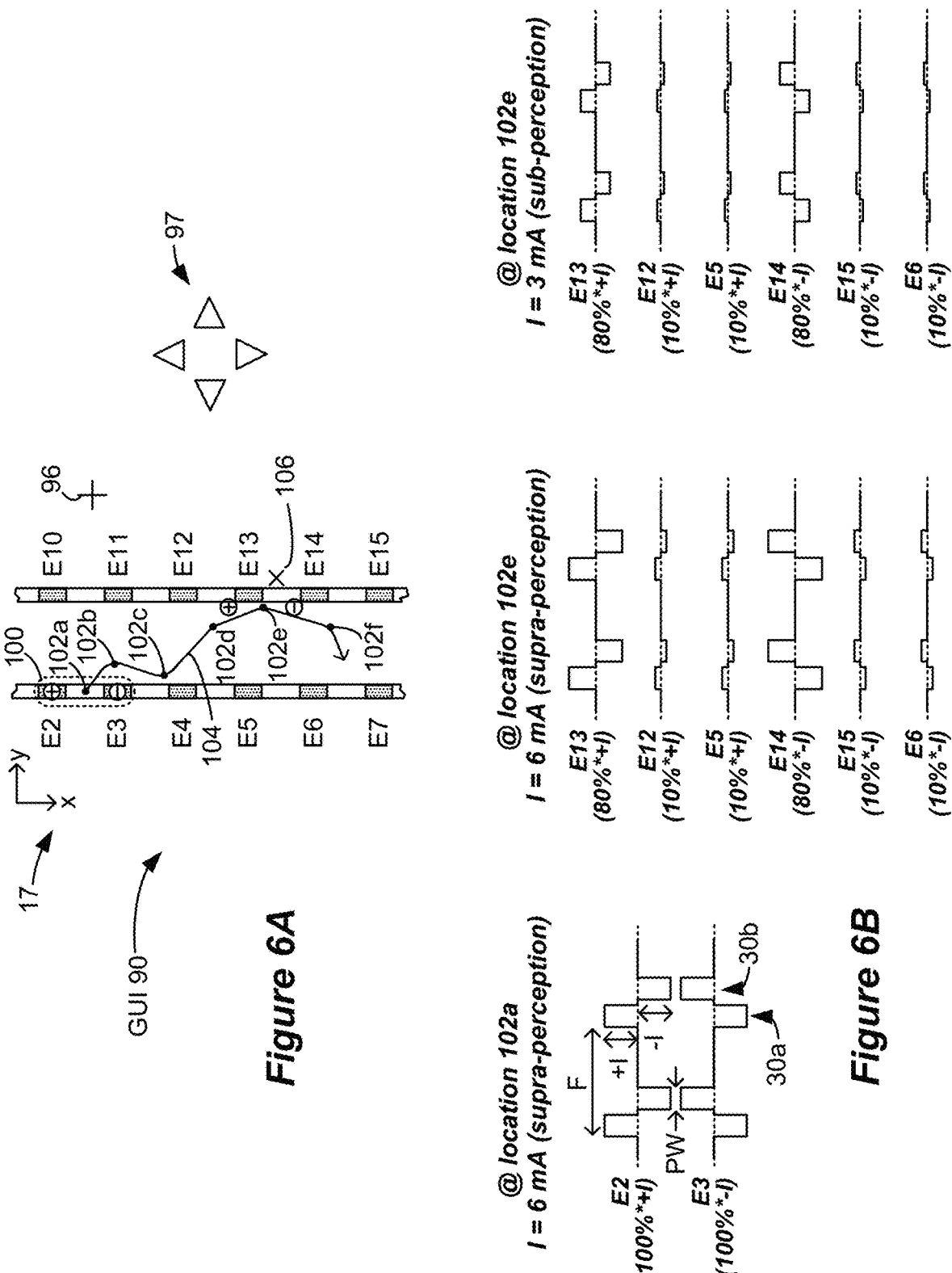
FIGS. 6A-6B show supra-perception sweet spot searching to determine an effective location in the electrode array to provide (preferably) sub-perception stimulation to a patient.

Sweet spot searching as disclosed in the '105 Publication is summarized in FIGS. 6A and 6B. Stimulation is initially provided as a supra-perception bipole 100 comprising an anode pole (+) and a cathode pole (−) formed in the electrode array 17. Even though the bipole 100 creates a three-dimensional electric field in the patient's tissue, it can still be defined as having a particular (x,y) location 102a in the electrode array 17. This location can be defined in different ways (e.g., a position of the anode pole or cathode pole, or relative to those points; a position within the electric field, etc.), but for simplicity the location 102a is defined as the center point between the anode and cathode poles. Once the bipole 100 is defined, this location 102a for the bipole can be set in GUI 90 in different ways. For example, directional arrows 97, cursor 96, or a joystick connected as a peripheral device to the external system can be used to set or move the location. The size and shape of the supra-perception bipole can be varied, as discussed further in the '105 Publication, and other supra-perception pole configurations (e.g., tripoles) could be used as well.

An electrode configuration algorithm operable as part of the clinician programmer software 86 (FIG. 4) can be used to automatically select electrodes to provide stimulation to place the bipole at the specified location 102a. This algorithm is explained in detail in U.S. Pat. No. 10,881,859, which is incorporated by reference in its entirety. By way of review, the electrode configuration algorithm determines the position of the anode and cathode poles relative to the location 102a, and selects electrodes as necessary to approximately place the anode and cathode poles at appropriate positions. For example, location 102a has been set directly between electrodes E2 and E3. If it is assumed that the bipole 100 has a separation distance (focus) between the anode and cathode pole equal to the distance between these electrodes, then the anode and cathode poles would be positioned exactly at electrodes E2 and E3. Thus, to locate the bipole 100 at location 102a, the electrode configuration algorithm would select only these electrodes to provide the entirety of the anodic (100%*+I, at E2) and cathodic (100%*−I, at E3) currents during first pulse phases 30a, as shown in FIG. 6B. Note also that these during phase 30b the polarities of these selected electrodes are reversed, which would place the anode pole at E3 and the cathode pole at E2. As explained farther below, the poles may also be placed at positions between the physical electrodes, in which case the electrode configuration algorithm may cause the anodic and cathodic currents to be shared, as explained further below.

Figure 3:
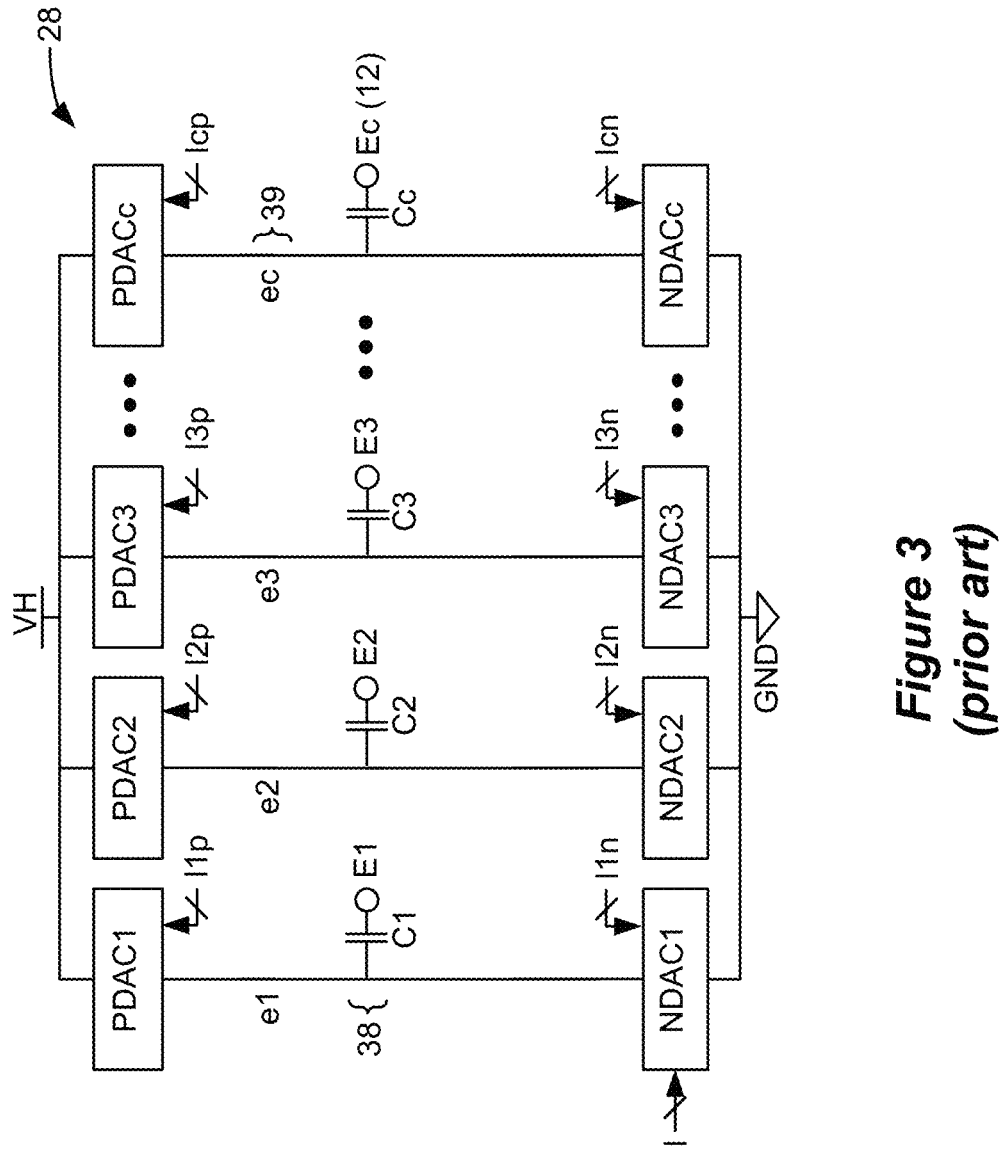
FIG. 3 shows stimulation circuitry used in the IPG to produce the stimulation pulses, in accordance with the prior art.

As discussed above, the bipole 100 at location 102a is supra-perception, which is most easily achieved by increasing the stimulation parameter of amplitude to a point that the patient can comfortably feel. This supra perception amplitude is assumed to be I=6 mA for the patient in the example of FIGS. 6A and 6B, but may be set to a different magnitude depending on the patient. Once the electrode configuration algorithm has determined the active electrodes, polarities, and relative percentages to form stimulation at location 102a, it can transmit instructions to the IPG 10 to form the supra-perception bipole 100. In this regard, the stimulation circuitry 28 described earlier (FIG. 3) is particularly useful because it allows the amplitudes and polarities of the currents to be independently set at each of the electrodes as per the electrode configuration algorithm.

After assessing the effectiveness of supra-perception bipole 100 at position 102a for the patient, the bipole may then be moved to new locations 102b, 102c, etc. in the electrode array 17 and similarly assessed. The electrode configuration algorithm would select new electrodes, polarities, and relative percentages to position the anode and cathode poles consistently with these new locations. As shown, the bipole is moved along a path 104 in FIG. 6A, which may be random or follow or set pattern.

It is assumed in this example that placing the supra-perception bipole 100 at location 102e provides the best therapeutic result for the patient, presumably because this bipole best covers and recruits a neural site of pain 106 in the patient's tissue. The waveforms as necessary to place supra-perception bipole 100 at this location 102e, as determined by the electrode configuration algorithm, are shown in FIG. 6B. Notice that the anode pole is close to electrode E13, but also somewhat proximate to electrodes E12 and E5. As a result, the electrode configuration algorithm has determined that E13 should receive a largest percentage of the anodic current (80%*+I), with electrodes E12 and E5 receiving less of this current (with each receiving 10%*+I). This creates the anode as a virtual pole with a position not directly at any of the physical electrodes. Similarly, the electrode configuration algorithm has selected certain electrodes (E14, E15, E6) to act as cathodes and to share the cathodic current to virtually place the cathode pole at the proper location in accordance with location 102e (with most-proximate electrode E14 receiving the highest share of the cathodic current –I, etc.). Again, the polarity of the currents is flipped at these selected electrodes to form the second pulse phases 30b. Because the bipole 100 is still supra-perception, notice that the amplitude (I=6 mA) may not be changed. However, this is not strictly necessary, and the amplitude can be adjusted at each new tested location 102i along path 104 to ensure that it is comfortably supra-perception for the patient being assessed.

Once an optimal location such as 102e has been determined for the patient, the stimulation at this location can be adjusted to a sub-perception level that the patient can no longer feel. As shown in FIG. 6B, this can involve reducing the amplitude (e.g., to I=3 mA in this example) while keeping the same electrode configuration (the same active electrodes, polarities, and relative percentages) determined earlier at location 102e, as shown in the waveforms of FIG. 6B. Of course, the sub-perception therapy can be further modified at this point if desired. For example, the frequency or pulse width can be adjusted.

It is expected that the sub-perception stimulation once determined at location 102e can then be used therapeutically by the patient going forward, and the '105 Publication explains advantages. For example, the frequency provided by the sub-perception pulses may be relatively low (e.g., 40-200 Hz), which is much more energy efficient than other prior art approaches using higher frequencies to provide sub-perception stimulation therapy. This means the battery 14 in the IPG 100 will last longer, or not require as frequent recharging. Furthermore, using a symmetric biphasic waveform is theorized to provide stimulation at two locations (e.g., the location of the cathode poles during each of the phases 30a and 30b), thereby improving coverage.

While the '105 Publication's approach of determining effective sub-perception therapy is beneficial, the inventors notice room for improvement and certain possible shortcomings. For one, the supra-perception sweet spot searching as just described can very well target the neural pain site 106, because the location 102i of the stimulation can be very finely adjusted in the electrode array 17 (e.g., in tenths of a millimeter). But such precise targeting of the stimulation can also have drawbacks related to the dynamic nature of the implantation environment is considered. Many factors can cause stimulation that is well targeted to become mistargeted over time. The leads 15 comprising the electrode array 17 can move or migrate in the spinal column over time, and hence move the position of the stimulation relative to the spinal tissue, and hence relative to the neural pain site 106. The patient can also move or place themselves in certain positions (e.g., supine prone, etc.), which likewise move the leads within the spinal column. Still further, involuntary movements such as patient respiration and pulsation relating to the patient's heart beating can cause transient shifts in the leads relative to the spinal column. This means that an optimal location determined for sub-perception stimulation, such as 102e, may not stay optimal as a function of time.

Obviously, an optimal location for stimulation in the electrode array 17 can be redetermined from time to time to address this issue. However, this can involve significant time, and usually requires the patient to visit the clinician's office so that the location of the stimulation can be moved. Such clinician intervention may even require repeating the entire sweet spot search in its entirety.

As a solution to this issue, the inventors have devised external system software and related algorithms to automatically vary as a function of time the location at which stimulation is applied to the patient. Such software can be executed on any external system for communicating with the IPG. As explained further below, location variation preferably occurs in a two-dimensional area defined with reference to the electrode array, although one-dimensional variations are also contemplated although not further discussed. The stimulation location may be varied within the area may occur randomly, or by setting a pre-defined path that varies the location within the area. Preferably the area is defined around a single location determined to be optimal for the patient, such as by using the sweet spot searching technique just discussed. Parameters relating to the area (e.g., its size and shape) and to how often the stimulation is moved (e.g., per a time interval Δt) can be set automatically or manually by a user of the software. Preferably, the area is defined using a probability distribution function (PDF) that tends to keep the stimulation at or close to an optimal location, while still allowing the stimulation location to be moved anywhere in the area. The area may also be defined in the software using measured parameters indicative of the effectiveness of stimulation at different locations, such as subjective measurements (e.g., patient pain scores) and/or objective measurements (e.g., measured neural responses to stimulation). The external system may determine area information and may periodically update and transmit new stimulation locations within the area to the IPG, or the external device may program the IPG with the area information to enable the IPG to move the stimulation locations within the area without external system assistance.

Moving the location of stimulation within the above-described area is useful to address the reality that initially well-targeted stimulation may not eventually well treat a neural pain site due to movement of the electrode array 17/leads 15 within the spinal column, whether due to patient movement, migration of leads, and the like. If such non-idealities occur, moving the location of stimulation within the area increases the probability of locating the stimulation proximate to the neural pain site, at least for some portion of the time. Such partial recruitment of a neural pain site may be acceptable to provide a patient with significant pain relief. As explained in the above-referenced '105 Publication, well-targeted sub-perception therapy can be advantageous in that such therapy tends to provide relief even after the sub-perception therapy has ceased. Said differently, the therapeutic benefits provided by sub-perception stimulation take some time to "wash out" after the therapy has ceased. In this regard, if the sub-perception is located within the area to well target the neural pain site for at least a portion of the time, effective therapy should still be provided even during times when the stimulation location is temporarily moved within the area to a location that does not well target the neural pain site.

Figure 7:
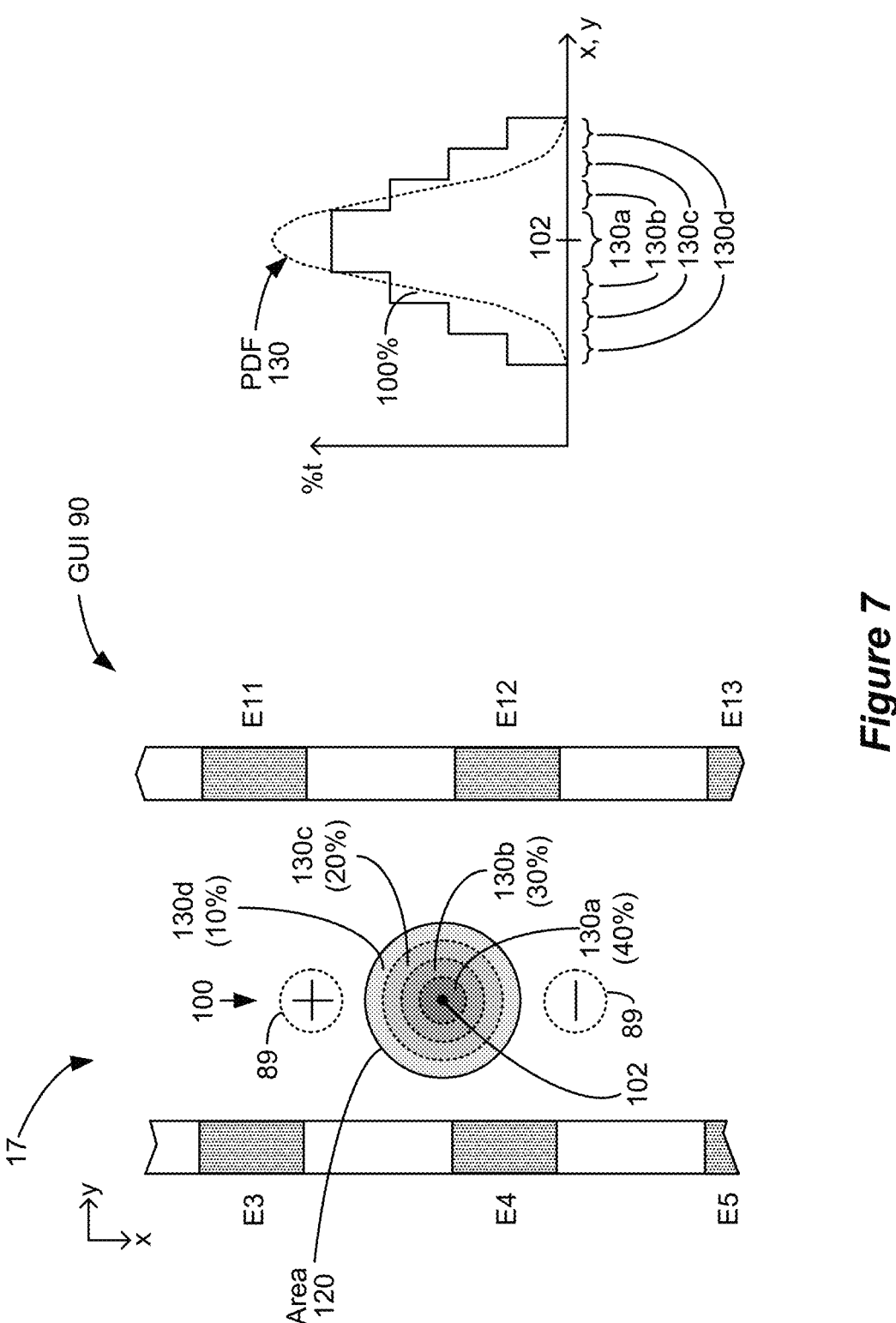
FIG. 7 shows an optimal location for stimulation for a patient in an electrode array, and an area within which stimulation can be automatically moved in accordance with an example of the invention, and additionally shows a probability distribution function (PDF) that can be used to weight stimulation locations within the area.

A first example of an area 120 of stimulation locations definable in the software is shown in FIG. 7. This area 120 once defined may be display as part of external system GUI 90 as explained earlier. As will be explained later, the GUI 90 can include further options and selections that allow the area 120 to be set in different manners. This example assumes that stimulation is provided to the patient as a bipole 100, and the location of anode (+) and cathode (−) poles 89 within bipole 100 are shown in the electrode array 17 as described earlier, and with reference to an optimal location 102. Optimal location 102 for the stimulation provided by bipole 100 can be determined in different manners, and preferably is determined using the supra-perception sweet spot search described earlier, although this isn't strictly necessary. The stimulation provided by bipole 100 may be sub-perception as described earlier (even if determined supra-perception).

In the example shown in FIG. 7, the area 120 is defined using a Probability Distribution Function (PDF) 130, which is shown graphically to the right. This PDF 130 (or "function" more generally) indicates probabilities that the stimulation will be located at a particular locations within area 120 as the stimulation is automatically moved within area 120. Preferably, the PDF provides higher probabilities at locations closer to the optimal location 102. For example, a sub-area 130a at a small radius around optimal location 102 has a relatively high percentage (e.g., 40%), as indicated by dark shading; a sub-area 130b at a larger radius has a smaller percentage (e.g., 30%) as indicated by lighter shading; and so on (130c at 20%; 130d at 10%). Notice that the PDF 130 that tends to keep the stimulation at or close to the optimal position 102, while still allowing the location to be set anywhere in the area 120. The PDF 130 can set probabilities radially symmetrically with respect to optimal location 102. However, this is not strictly necessary, and the PDF 130 can instead be radially asymmetric, or asymmetric in x- and y-directions, etc., as shown in some examples later. While it is easiest here to illustrate PDF 130 with reference to discrete sub-areas 130i, the PDF 130 may also set probabilities using a mathematical formula. For example, the PDF 130 can also be defined per a well-known normal (Gaussian) distribution, as shown in dotted lines in the graph at right, or by using any other mathematical function. PDF 130 may also comprise a table in which positions within area 120 are assigned to different probability values. Preferably, the PDF 130 comprises at least two different probability values for different positions in area 120 that are greater than 0% and less than 100%.

Figures 8A, 8B:
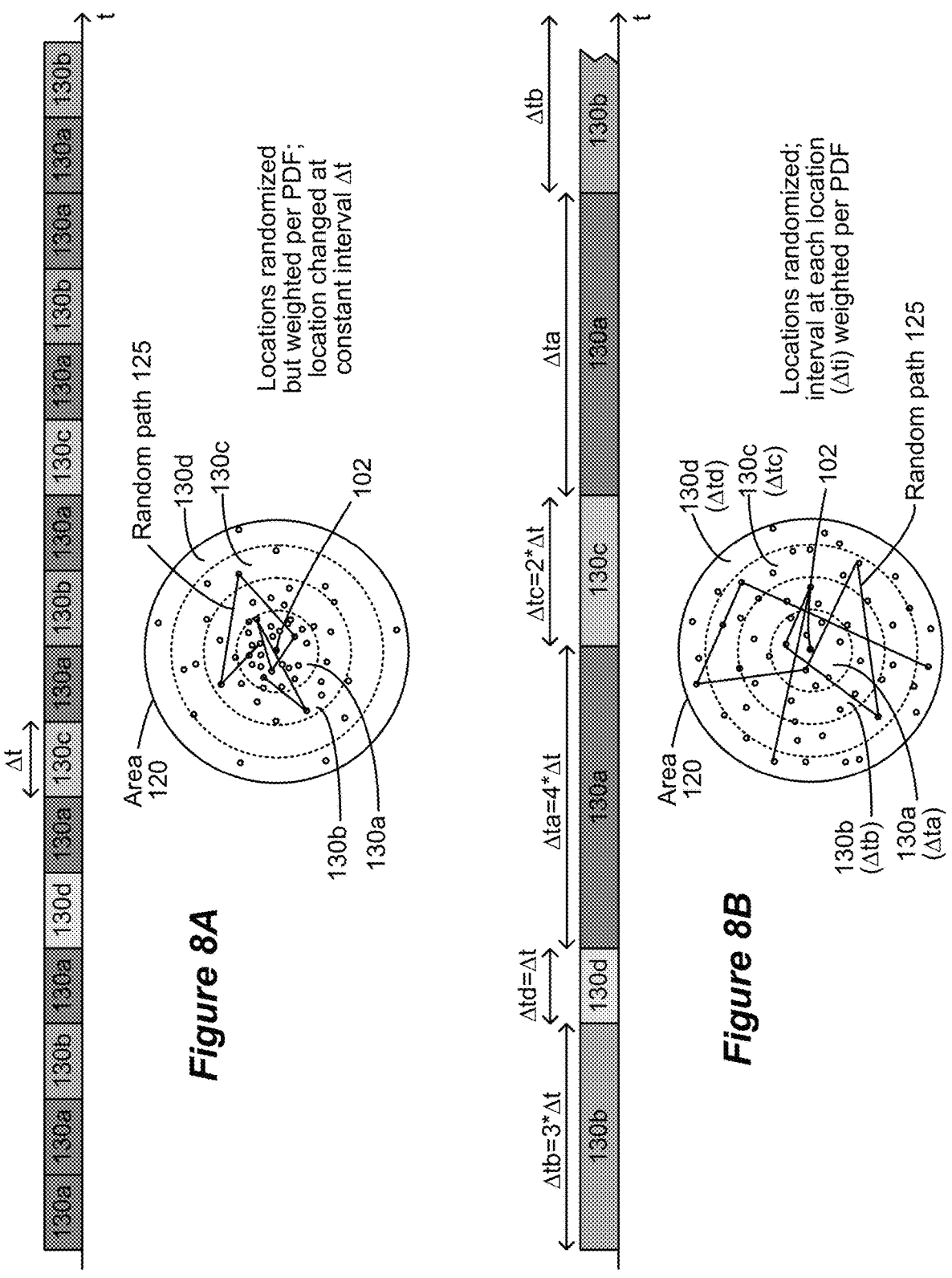
FIGS. 8A and 8B show different examples of use of a PDF to influence the selection of random locations for stimulation within an area.

FIGS. 8A and 8B show different examples of how the software can vary the location of the stimulation within the area 120 using PDF 130. In this graph, each of the points comprises a new location set for the stimulation. In FIG. 8A, it is assumed that the stimulation location is automatically periodically and randomly changed in accordance with a time interval Δt, causing the location to follow a random path 125. Time interval Δt can be set by the user of the software as explained later. It would be expected that this time interval would be set to move the location on the order of seconds to minutes, although other time scales are possible.

In this example, although new locations are randomly chosen, the PDF 130 weights this random selection to preferentially select locations that have higher probabilities and that are more proximate to the optimal location 102 around which the area 120 is set. As such, the points (locations) tend to cluster around optimal location 102, i.e., most locations are within sub-area 130a, then 130b, etc. The use of PDF 130 is sensible in this regard: it tends to select locations for stimulation that are close to optimal (102), while also statistically allowing the stimulation to some-times be located somewhat distantly from this optimal location. As noted earlier, this is useful to cover the contin-gency that the electrode array 17/leads 15 have moved relative within the spinal column, because it would be expected that at least some stimulation locations distant from optimal location 102 will still well recruit the neural pain site. Note that once a new stimulation location is automatically selected by the software, the electrode con-figuration algorithm described previously will operate to locate the poles 89 consistent with this new location (e.g., by selecting active electrodes, polarities of those active elec-trodes, and the relative contributions of those electrodes).

FIG. 8B also uses PDF 130 to preferentially apply stimu-lation proximate to optimal location 102. However, unlike FIG. 8A, the PDF 130 in FIG. 8B is used to set how long the stimulation is applied at particular locations once they have been randomly selected, i.e., to set a relative time at which stimulation will be applied at locations within the area 120. For example, if a location is randomly selected that is closer to optimal location 102 (e.g., within sub-area 130a), the weighting provided by PDF 130 is used to hold the stimu-lation longer at these locations (e.g., Δta=4*Δt). By contrast, if a location is randomly selected that is far from optimal location 102 (e.g., within sub-area 130d), the weighting provided by PDF 130 is used to hold the stimulation shorter at these locations (e.g., Δtd=Δt). Notice then that FIGS. 8A and 8B are similar in effect in that the PDF 130 favors over time setting the stimulation location closer to the optimal location 102.

FIGS. 9A and 9B show other examples in which a PDF 130 can be used to vary stimulation within area 120. In these figures, the software does not select stimulation locations within area 120 at random. Instead, stimulation locations are pre-selected using a pre-defined path 140. In this example, this path 140 moves the stimulation locations along the pre-defined path 140 in a radially serpentine fashion, but this is just one example and different pre-defined paths could be used to place the stimulation locations within area 120. In FIG. 9A, the stimulation locations are moved in accordance with a set time interval, Δt, similar to what occurred earlier in FIG. 8. However, the PDF 130 is used to weight the placement of locations pre-defined path 140, with more stimulation locations being placed along the path at locations (e.g., sub-area 130a) proximate to the optimal location 102, and fewer stimulation locations being placed along the path at locations (e.g., sub-area 130d) farther from the optimal location 102.

FIG. 9B also uses a predetermined path 140 with set stimulation locations. However, and similarly to FIG. 8B, the PDF 130 in FIG. 9B is used to set how long the stimulation is applied at particular locations once they have been randomly selected. For example, for locations along the path 140 that are closer to optimal location 102 (e.g., within sub-area 130a), the weighting provided by PDF 130 is used to hold the stimulation longer at these locations (e.g., Δta=4*Δt). By contrast, for locations along the path 140 that are farther from optimal location 102 (e.g., within sub-area 130a), the weighting provided by PDF 130 is used to hold the stimulation for shorter times at these locations (e.g., Δtd=Δt).

Figures 10, 11:
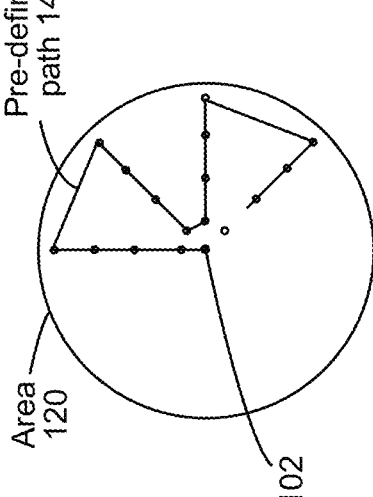
FIGS. 10 and 11 show different examples in which stimulation can be moved in an area without use of a PDF.

Use of a PDF 130 to preferably set higher probabilities to set the location of stimulation within area 120 to locations closer to the optimal location 102 are beneficial, but not strictly required in all examples of the invention. FIGS. 10 and 11 show other examples in which the stimulation location can be varied by the software, without use of a PDF 130. In FIG. 10, the location of stimulation is randomly set, and moved at a constant time interval, Δt, thus moving the stimulation along within area 120 random path 125. FIG. 11 shows moving the stimulation locations within area around a pre-defined path 140.

Figure 4:
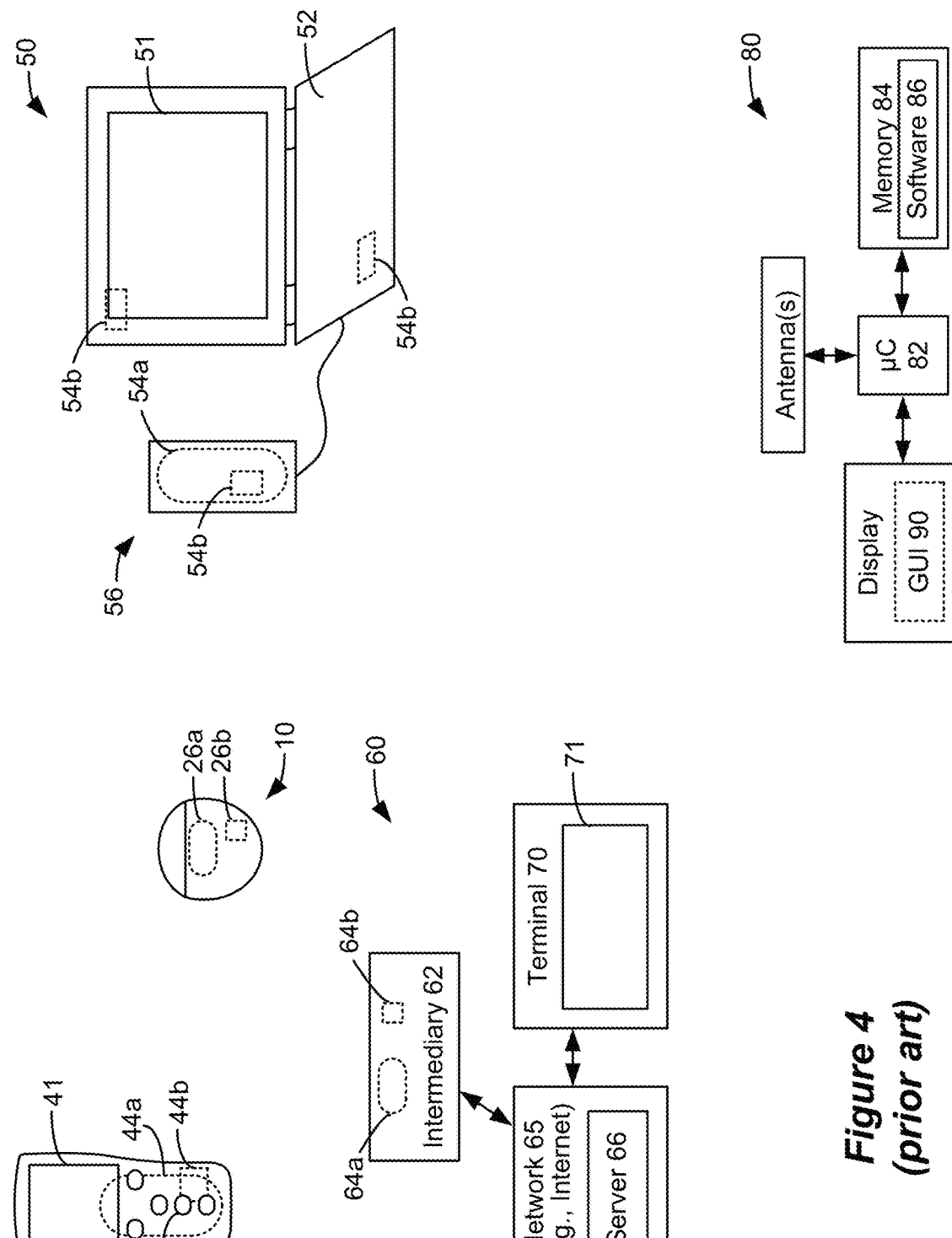
FIG. 4 shows various external systems capable of communicating with and programming stimulation in an IPG, in accordance with the prior art.
Figure 12:
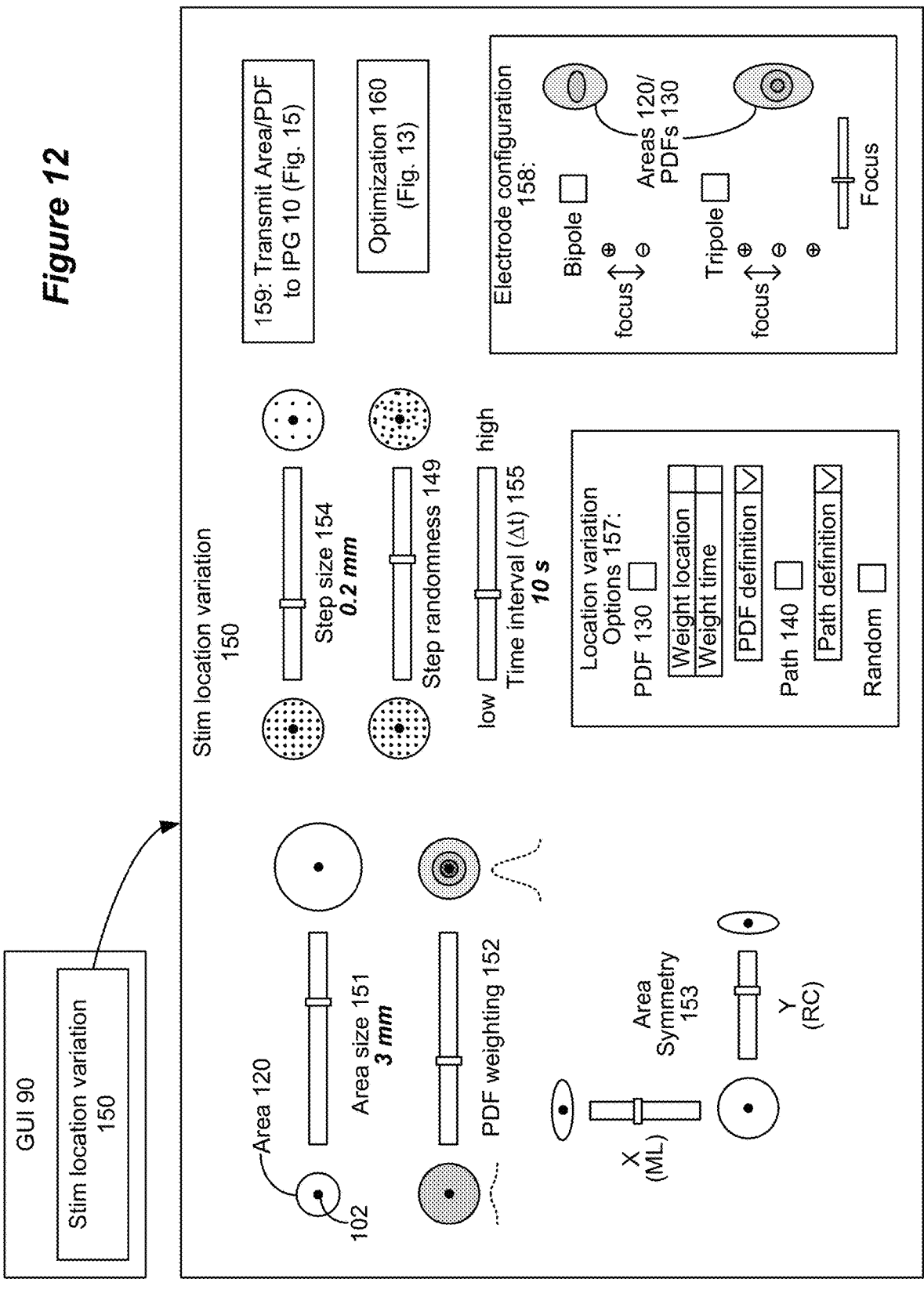
FIG. 12 shows a GUI used to select various options that allow an area and PDF to be defined.

FIG. 12 shows how stimulation location variation as just described can be enabled in the external system software. As noted earlier, such software involves use of a GUI 90, which can be rendered on a display associated with an external system, such as the external controller 40, clinician programmer 50, or a network-based system (FIG. 4). Aspects shows in FIG. 12 can be included as part of the external system software 86 (FIG. 4). The GUI 90 as shown can include an option 150 to allow stimulation location variation around an optimal location 102 to be prescribed. In FIG. 12, it is again assumed that an otherwise optimal stimulation location 102 around which variation will occur has already been established.

Selection of option 150 allows stimulation location variation within an area 120 to be set and defined in different manners. For example, option 151 allows the basic size of the area 120 to be set. In the example shown, area size is shown as a radius of the area 120 around optimal location 102, but area 120's size could be set in different ways. In the depicted example, the size can be selected or adjusted using a slider, although one skilled in the art will understand that other means providable in a GUI may be used to select or adjust the size as well as other features in FIG. 12 (e.g., increase or decrease buttons, check boxes, text entry, drop down menus, etc.). The selected size may be shown textually (e.g., 3 mm) in the GUI 90 for the user's convenience.

Option 152 allows the degree of weighting to be set by for the PDF 130. (Such an adjustment may only be provided if the user has selected to use a PDF under options 157, as explained below). Using a slider for example, the user can select whether to more or less heavily concentrate the use of stimulation locations proximate to the optimal location 102.

Option 153 allows the symmetry of area 120 to be modified, and includes separate sliders to adjust the size of the area 120 in x and y directions, thus allowing area 120 to be formed with a more oval shape as shown. This is particularly useful in an SCS application, because it may be more important for a given patient that the stimulation be allowed to move within area 120 in a more rostral-caudal (RC; head to toe) direction or a more medio-lateral (ML; left to right) direction. This is useful, because it may be desirable to elongate the area 120 in a rostral-caudal or a medio-lateral direction. Still other GUI options may allow the shape of area 120 to be set. For example, area 120 can be rectangular, with the user selecting the dimensions of this rectangular area.

Option 154 allows the step size of stimulation adjustments to be adjusted, which can comprise a minimum distance that the stimulation location can be moved within the area 120, and which therefore generally sets the granularity for movement of the stimulation locations. Option 149 allows the locations to where stimulation can be moved within the area 120 to be defined more regularly (e.g., on a regular grid or radial pattern) or more randomly. Option 155 allows the user to set the time interval Δt with which the stimulation will be moved. See FIGS. 8A and 8B. This time interval may be varied by use of a PDF 130 in some example, as explained earlier with respect to FIGS. 8B and 9B.

Option 157 presents various options that specify how the stimulation location can be moved within the area 120, and these options can be used in different combinations. For example, the user can choose to apply a PDF 130, which again can be used to increase the probability that stimulation will be moved to locations within area 120 that are more proximate to optimal location 102. See FIGS. 8A-9B. The GUI 90 may also include an option to allow the user to define the PDF 130, e.g., to set the boundaries of sub-areas 130i and their percentages; to set a mathematical function (e.g., Gaussian); and/or to otherwise selected a particular PDF for use. For example, this option may be used to select use of a particular PDF determined for the patient using a patient optimization option 160, explained further below. A drop-down option is shown for this, although PDF can be defined or selected in the GUI 90 in different ways. Still further options may be included to allow the PDF weight to the selection of next locations (e.g., FIGS. 8A, 9A) or to weight the time that stimulation is provided at otherwise-randomly selected next locations (e.g., FIGS. 8B, 9B).

Option 157 may also include options to select how the stimulation will be moved with the area 120, such as by a pre-defined path 140 (e.g., FIGS. 9A, 9B, 11) or at random (FIGS. 8A, 8B, 10). As discussed earlier, these options can be used with (FIGS. 8A-9B) or without (FIGS. 10, 11) use of a PDF 130. The GUI 90 may also allow the user to set the predefined path 140, and again a drop-down option is shown to allow different paths to be selected or defined. Note that the path definition option may automatically set other parameters in the GUI 90, such as the step size (154), randomness (144), and/or time interval Δt. Further, and more generally, setting or selecting one option in GUI 90 may affect or automatically set other GUI settings as well.

Options 158 allow the area 120, and possibly an associated PDF 130, to be defined based on a pole configuration (e.g., bipole, tripole, etc.) that is being used for the patient's stimulation. This is beneficial because different pole configurations may benefit from different shaped areas 120 and/or from different PDFs 130. The area 120 may also depend on the distances that separate the poles in the pole configurations, what is sometimes known in the art as the pole's "focus." As such, option 158 may allow this focus (distance) to be adjusted and to define area 120 accordingly. Once the area 120 and/or PDF 130 has been defined in the GUI, information indicative of these aspects can be transmitted to the IPG 10 (option 159) for execution and to allow the stimulation location to be varied, as discussed further below with reference to FIG. 15.

A patient optimization option 160 is also shown in FIG. 12, with FIG. 13 showing details provided by the GUI 90 after its selection. The optimization option allows the area 120 to be tailored for the patient based on measured parameters indicative of the effectiveness of stimulation at different locations. Such tailoring can involve both setting the boundaries for area 120 as well as determining a PDF 130 which will dictate the probabilities of movement of stimulation within the area. The optimization interface shown in FIG. 13 allows a user select and test various locations, and in the example shown four test locations have been assessed M1-M4. These locations are preferably generally proximate to the optimal location 102 determined earlier, and are shown in this example as forming a square around location 102. However, this is just an example, and more or fewer test locations could be assessed. As noted, measurements indicative of the effectiveness of stimulation therapy at these test locations can be taken and entered into the GUI 90. A table 165 is shown for this purpose, although other means of entering and associating the measurements with the test locations can be used occur.

The measurements can be subjective or objective in nature, and table 165 show examples of both types of measurements. Subjective measurements are those determined by observation or based on user or patient feedback. For example, a subjective measurement can comprise a patient rating of their symptoms, such as pain, and in this example a rating scale from 1 (good) to 10 (poor) is used. Another subjective measurement can comprise a patient's assessment of how well stimulation at a location seems to be covering his symptoms, with higher percentages indicating better therapeutic results. Objective measurements are not based on subjective feedback, and instead are measured by equipment, such as perhaps by the IPG itself. One example of an objective measurements comprises Evoked Compound Action Potentials (ECAPs) that are evoked in the spinal tissue in response to the stimulation. The reader's familiarity with measurement of ECAPs in an SCS system is assumed. See, e.g., PCT (Int'l) Patent Application Publication WO 2020/223165, which is incorporated herein by reference. One objective measurement may comprise a particular feature of sensed ECAPs, such as their amplitude (in µV), and this example is populated in table 165, with larger amplitudes indicating better spinal tissue recruitment and therefore better therapeutic results. Again, this is just one example of an objective measurement that may be taken when stimulation is provided at the various test locations. Note that measurements taken when stimulation is at the optimal location 102 may be included in table 165 as shown in dotted lines, and these measurements may already have been determined based on prior testing.

Once measurements have been populated in table 165 for each of the test locations, an option 167 on the GUI 90 may be selected to use the measurement data to determine an area 120 for the patient in which stimulation will be moved. All measurements in table 165 could be used to determine the area 120, but for simplicity FIG. 13 only considers the subjective measurement of patient pain score. As shown at the bottom, the patient reports best results (lowest score, 3) when stimulation is located at the optimal location 102; slightly worse results (4) when stimulation is located at test location M1; still worse results (5) at test locations M2 and M3; and the worst result (6) at test location M4.

These measurements can be used by the software to automatically determine an area 120 for the patient in which stimulation can be moved. As shown in FIG. 13, this area 120 preferentially encompasses locations having better therapeutic measurements (102, M1), and may exclude locations (e.g., M4) having worse measurements. Still further, the software may use the measurements to determine a PDF 130. This is again shown in FIG. 13 by the use of sub-areas 130i defining probabilities for locating the stimulation. Notice for example that sub-area 130a having a highest percentage (60%) encompasses the optimal location 102 and tends towards better measurements (e.g., M1) and away from worse ones (e.g., M4). Lower percentage sub-areas (e.g., 130b and 130c) may also be defined asymmetrically towards better measurements. One skilled will understand that the border of area 120 and PDF 130 (sub-areas 130i) can be automatically determined in a number of different ways using the measurements, such as by determining the spatial gradient of the measurements at the various test locations. If multiple measurements are used (e.g., subjective and objective), they may be averaged or processed in some fashion to allow the area 120 and/or PDF 130 to be defined as best for the patient. Once a patient-optimized area 120 and or PDF 130 is determined for the patient, it may be applied and/or modified using the various options explained earlier with respect to FIG. 12.

Figure 14:
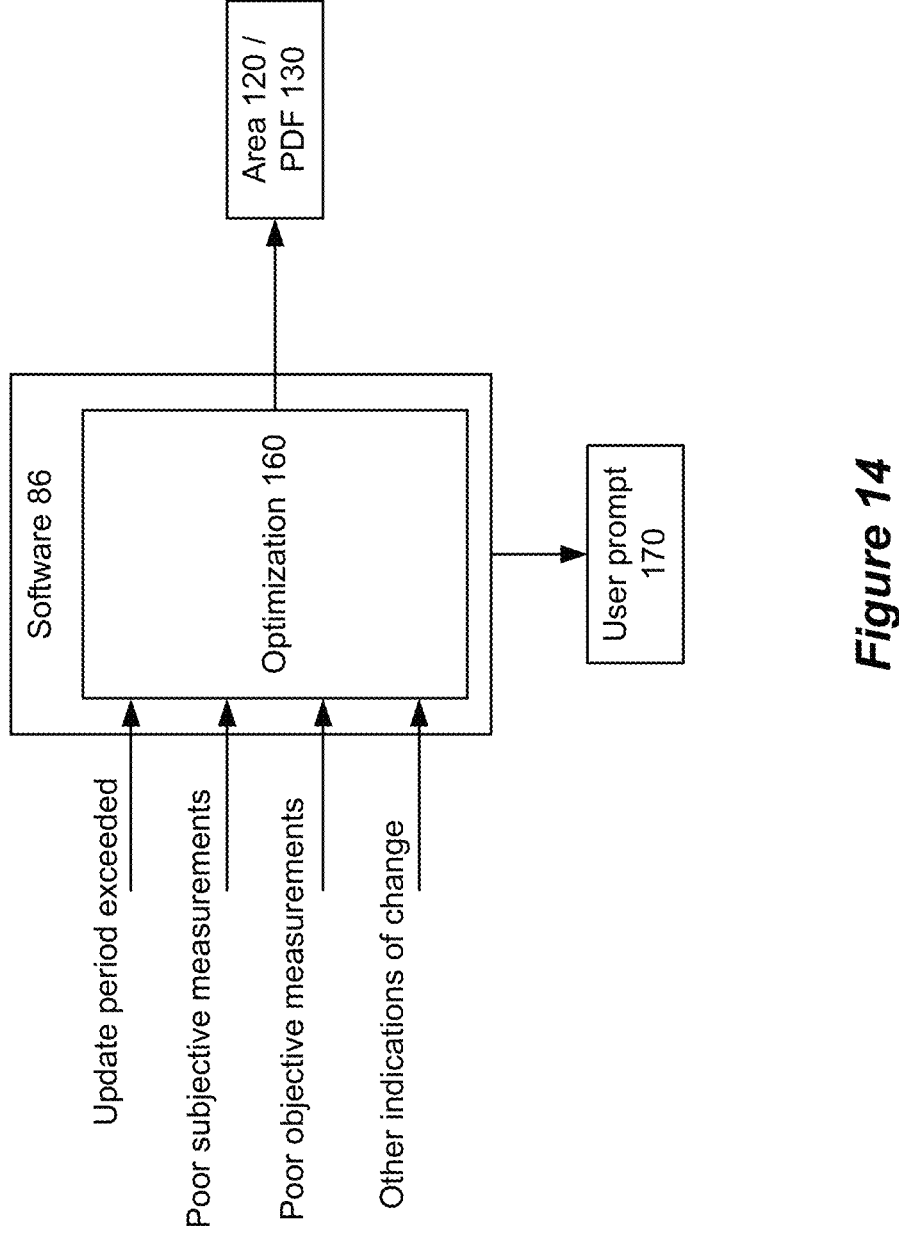
FIG. 14 shows various manners in which optimization per FIG. 13 can automatically occur.

While patient optimization option 160 is shown as a user-selectable option in the GUI 90, it may also be automatically initiated under various circumstances as described in FIG. 14 to determine or redetermine a PDF 130 and/or area 120 for the patient. This is sensible because circumstances may suggest that an initially-determined PDF 130 and/or area 120 may become less optimal in the future. For example, leads may have migrated over time, scar tissue may have formed, the patient may be having less success with the stimulation therapy, etc.

Optimization 160 therefore can occur at different points in time and under different circumstances to establish a PDF 130 and/or area 120 for the patient, or to update the PDF 130 and/or area 120. For example, and as shown in FIG. 14, optimization 160 can be automatically run (or re-run) after the external system software 86 understands that an update period has expired (e.g., 6 months). In another example, optimization 160 can be automatically (re)run after the software 86 receives an indication that subjective measurements indicative of therapy efficacy are poor, or otherwise less than optimal. These various subjective measurements were described above (pain scores, etc.), and optimization 160 can be (re)run if such measurements are below or exceed a threshold for example. Similarly, optimization 160 can be automatically (re)run after the software 86 receives an indication that objective measurements indicative of therapy efficacy are poor, or otherwise less than optimal. These various objective measurements were described above (ECAPs, etc.), and optimization 160 can be (re)run if such measurements are again below or exceed a threshold. Lastly, optimization 160 can also be automatically (re)run after the software 86 receives some other indication of significant changes that might affect the PDF 130 and/or area 120. Such other changes could comprise several different things determinable by the system of the IPG 100, such as changes in electrode impedance, changes in patient posture, etc.

Optimization 160 may run automatically when such circumstances are present, and may transmit information about the new PDF 130 and/or PDF 120 to the IPG 100 without further input from the user or patient, as discussed further below with respect to FIG. 15. However, because optimization 160 may require input from the patient (e.g., subjective measurements), the software 86 may prompt the user (e.g., on the display an external system) to select this option to allow a new PDF 130 and/or area 120 to be determined. Such a prompt 170 may explain the reason for running or re-running the optimization. Prompt 170 may be provided on the display on the external system where the software 86 is running, or may be telemetered to a different external system to allow for user input and telemetry back to the software. For example, if software 86 is running on the clinician programmer 50, the prompt 170 may be teleme- tered to the patient external controller 40, thus allowing the patient to input subjective measurements, which can be telemetered back to the clinician programmer 50 to allow PDF 130 and/or area 120 to be (re)ascertained.

Figure 15:
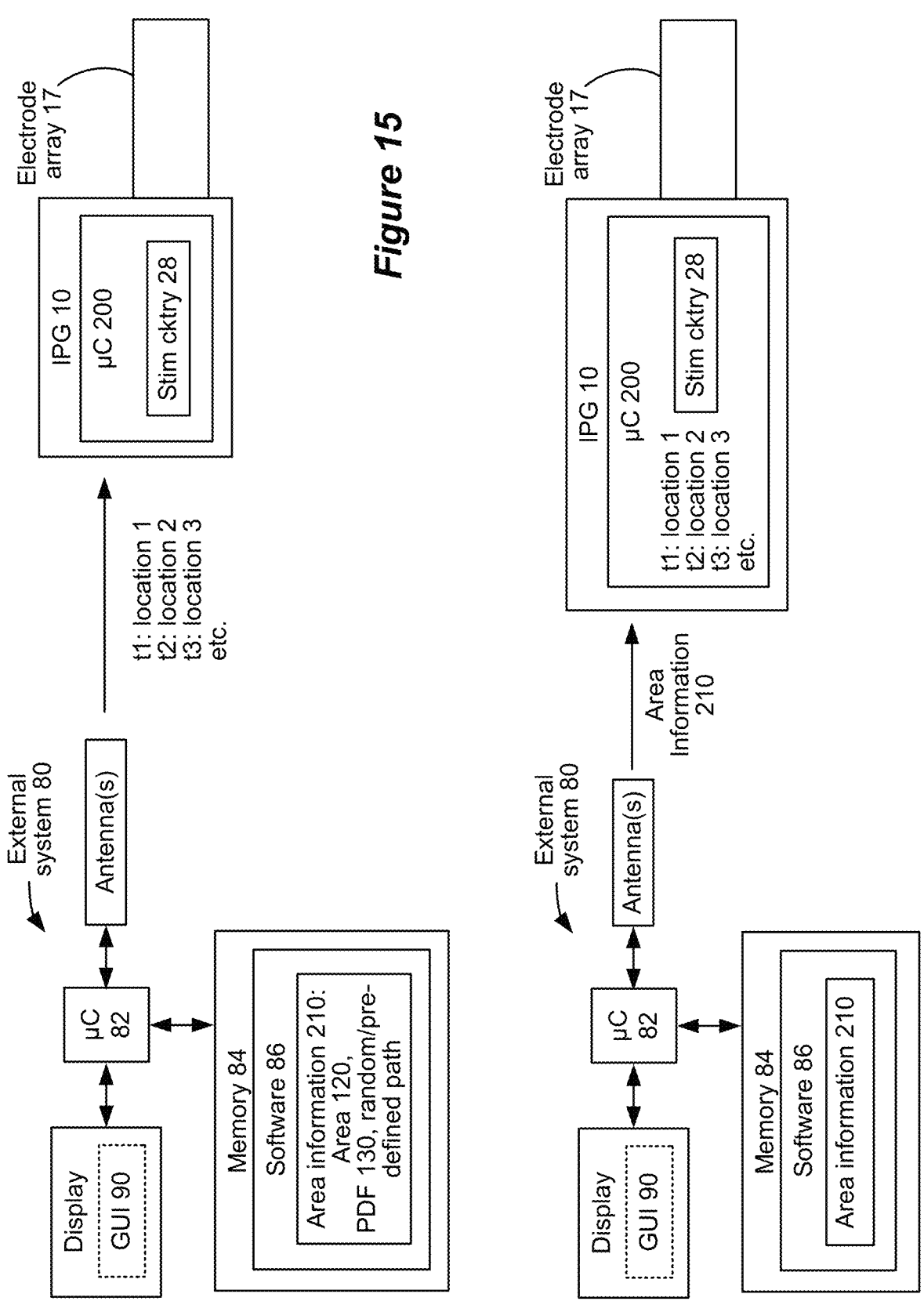
FIG. 15 shows different manners in which the external system and IPG can interact to affect movement of stimulation within an area.

FIG. 15 shows different manners by which area informa- tion 210 determined at an external system 80 can be imple- mented to automatically move the location of stimulation within an area 120 in a patient's electrode array 17. Such area information 210 may include the dimensions and size of the area 120, any PDF 130 used to dictate and weight stimulation location movement within the area, whether such movement will occur randomly or in accordance with a pre-defined path, and other stimulation location variation options discussed earlier and selected at the GUI 90. The top of FIG. 15 shows determining next locations for stimulation at the external system 80, and periodically transmitting these locations to the IPG 10. This example is beneficial in that processing is off-loaded to the external system 80, but requires the external system and the IPG 10 to be in periodic communication with each other. Periodic transmission of the locations doesn't necessarily require that these locations be transmitted at constant time intervals, but instead merely that they be transmitted from time to time. The bottom of FIG. 15 shows an example in which the area information 210 is transmitted to the IPG 10 and stored within its control circuitry 200. This allows the IPG's control circuitry 200 to periodically determine next stimulation locations in accor- dance with the area information 210. While this is compu- tationally more intensive for the IPG 10, it is beneficial because the IPG 10 and external system 80 are not required to be in constant communication to enable the IPG 10 to move the location of stimulation within the area 120.

Various aspects of the disclosed techniques, including processes implementable in the IPG or in external systems, can be formulated and stored as instructions in a non- transitory computer-readable media associated with such devices, such as in a magnetic, optical, or solid state memory. The computer-readable media may also comprise a device readable by such systems, such as a memory stick or a removable disk. The computer-readable media may also be associated with a server (66, FIG. 4) remote from other aspects of the system.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for providing stimulation in a stimulator device having a plurality of electrode nodes each coupled to an electrode in contact with a patient's tissue, wherein the electrodes form an electrode array, the method comprising: determining a first location in the electrode array to apply the stimulation for the patient; determining a function, wherein the function indicates probabilities of positioning the stimulation at locations within an area defined around the first location; and applying the stimulation to the patient using the electrode array by moving the location of the stimulation over time within the area in accordance with the function to locate the stimulation in accordance with the probabili- ties.

2. The method of claim 1, wherein the function indicates at least two different probabilities.

3. The method of claim 1, wherein the probabilities are greater than 0% and less than 100%.

4. The method of claim 1, wherein the probabilities preferentially locate the stimulation proximate to the first location when the stimulation is moved within the area.

5. The method of claim 1, wherein the probabilities set a relative time at which stimulation will be applied at loca- tions within the area.

6. The method of claim 1, wherein the stimulation is automatically moved within the area.

7. The method of claim 1, wherein the stimulation is moved at a constant time interval within the area.

8. The method of claim 1, wherein the stimulation is moved randomly among the locations within the area.

9. The method of claim 1, wherein the stimulation is moved to the locations within the area in accordance with a pre-defined path.

10. The method of claim 1, wherein the first location is at a center of the area.

11. The method of claim 1, wherein the function com- prises sub-areas within the area each associated with one of the probabilities.

12. The method of claim 1, wherein the function com- prises a mathematical function that determines the probabili- ties.

13. The method of claim 1, wherein the stimulation moved within the area is sub-perception.

14. The method of claim 1, wherein the first location is determined to provide effective therapeutic results for the patient.

15. The method of claim 1, wherein the function is determined using measurements indicative of the efficacy of the stimulation for the patient.

16. The method of claim 1, wherein the function is determined in an external system in communication with the stimulator device, and wherein information indicative of the function is transmitted to the stimulator device to enable the stimulator device to move the location of the stimulation within the area in accordance with the function.

17. The method of claim 1, wherein the function is determined in an external system in communication with the stimulator device, and wherein the locations to which the stimulation are moved are periodically transmitted to the stimulator device to enable the stimulator device to move the location of the stimulation within the area in accordance with the function.

18. The method of claim 17, further comprising updating the function, wherein the location of the stimulation is moved over time within the area in accordance with the updated function to locate the stimulation in accordance with the probabilities.

19. A system, comprising: an external system configured to control a stimulator device having a plurality of electrode nodes each coupled to an electrode contactable with a patient's tissue, wherein the electrodes form an electrode array, the external system comprising control circuitry configured to render a graphical user interface (GUI) to allow a user to:

input a plurality of stimulation parameters, whereby the GUI programs the stimulation device to produce stimulation for the patient at one or more of the electrode nodes;

select one or more options to move the stimulation in the electrode array to determine a first location for the stimulation;

determine a function, wherein the function indicates probabilities of positioning the stimulation at locations within an area defined around the first location; and transmit information to the stimulator device to cause the stimulator device to apply the stimulation to the patient by moving the location of the stimulation in the electrode array over time within the area in accordance with the function to locate the stimulation in accordance with the probabilities.

* * * * *